United States Patent [19]
Langton et al.

[11] Patent Number: 5,460,592
[45] Date of Patent: Oct. 24, 1995

[54] APPARATUS AND METHOD FOR MAKING CARRIER ASSEMBLY FOR RADIOACTIVE SEED CARRIER

[75] Inventors: Michael A. Langton, Elk Grove Village; Frank J. Lyman, Lake Zurich; Jay C. Reed, Elk Grove Village, all of Ill.

[73] Assignee: Amersham Holdings, Inc., Arlington Heights, Ill.

[21] Appl. No.: 186,448

[22] Filed: Jan. 24, 1994

[51] Int. Cl.$^6$ ................................................. A61M 36/00
[52] U.S. Cl. ........................................................ 600/7
[58] Field of Search ............................................ 600/1–8

[56] References Cited

U.S. PATENT DOCUMENTS

| | | | |
|---|---|---|---|
| 3,565,869 | 2/1971 | DeProspero | 260/78.3 |
| 3,636,956 | 1/1972 | Schneider | 128/335.5 |
| 4,052,988 | 10/1977 | Doddi et al. | 128/335.5 |
| 4,323,055 | 4/1982 | Kubiatowicz | 128/1.2 |
| 4,697,575 | 10/1987 | Horowitz | 128/1.2 |
| 4,815,449 | 3/1989 | Horowitz | 600/7 |

FOREIGN PATENT DOCUMENTS

| | | |
|---|---|---|
| 30822 | 6/1981 | European Pat. Off. . |
| 64860 | 11/1982 | European Pat. Off. . |

OTHER PUBLICATIONS

"Ultrasonically Guided Transperineal Seed Implantation of the Prostate: Modification of the Technique and Qualitative Assessment of Implants" by Van't Riet, et al., International Journal of Radiation Oncology, Biology and Physics, vol. 24, No. 3, pp. 555–558, 1992.
Medi–Physics brochure entitled "I–125 Seeds® In Carrier", Model No. 6720.
Medi–Physics brochure entitled "I–125 Seed® Source Model 6711".

Primary Examiner—Kyle L. Howell
Assistant Examiner—J. P. Lacyk
Attorney, Agent, or Firm—Marshall, O'Toole, Gerstein, Murray & Borun

[57] ABSTRACT

The method and apparatus for transporting a radioactive carrier device comprising flexible elongated bio-absorbable material having spaced radioactive seeds disposed therein in which the elongated material is loaded in a spacing jig member having spaced first recesses to accommodate the seeds and second recesses to accommodate the elongated material. The loaded jig member has a sheath shielding member placed over it. The carrier assembly is heated to make the carrier device non-deflecting. The carrier assembly, which is placed in a primary shipping container, also may be autoclaved prior to shipping the packaged assembly to a site of use.

33 Claims, 6 Drawing Sheets

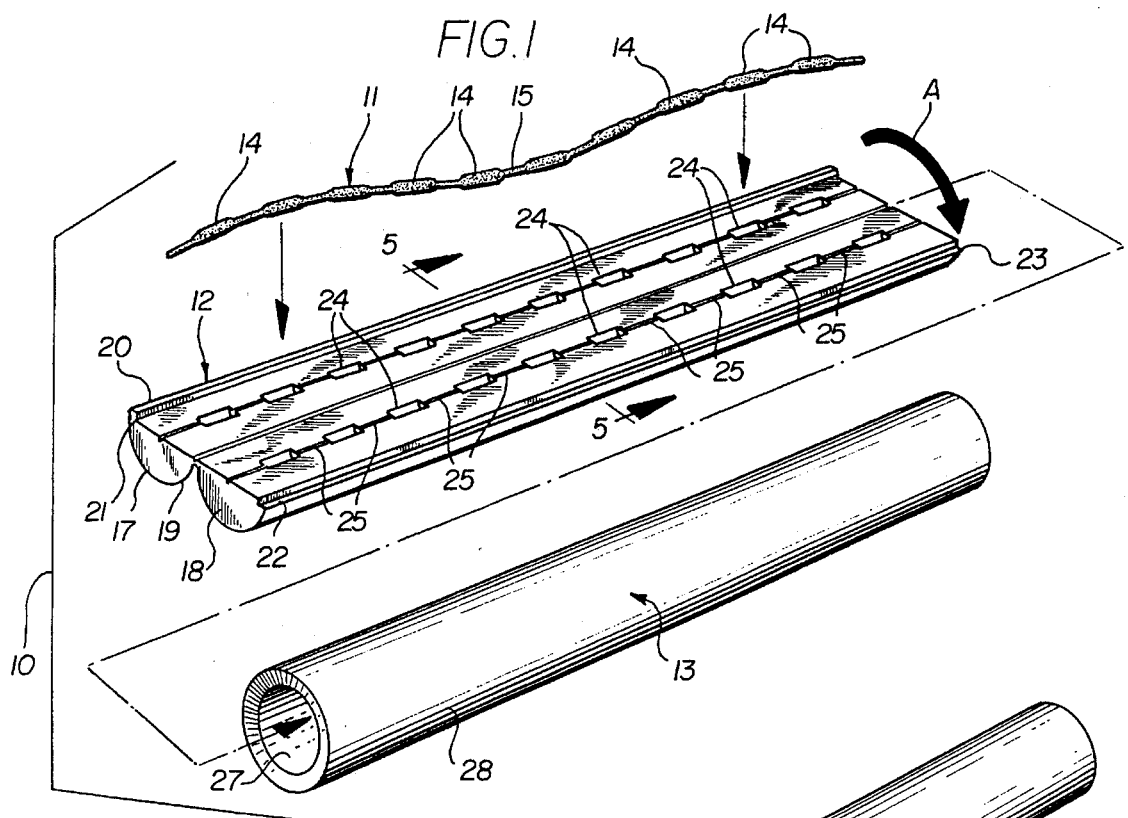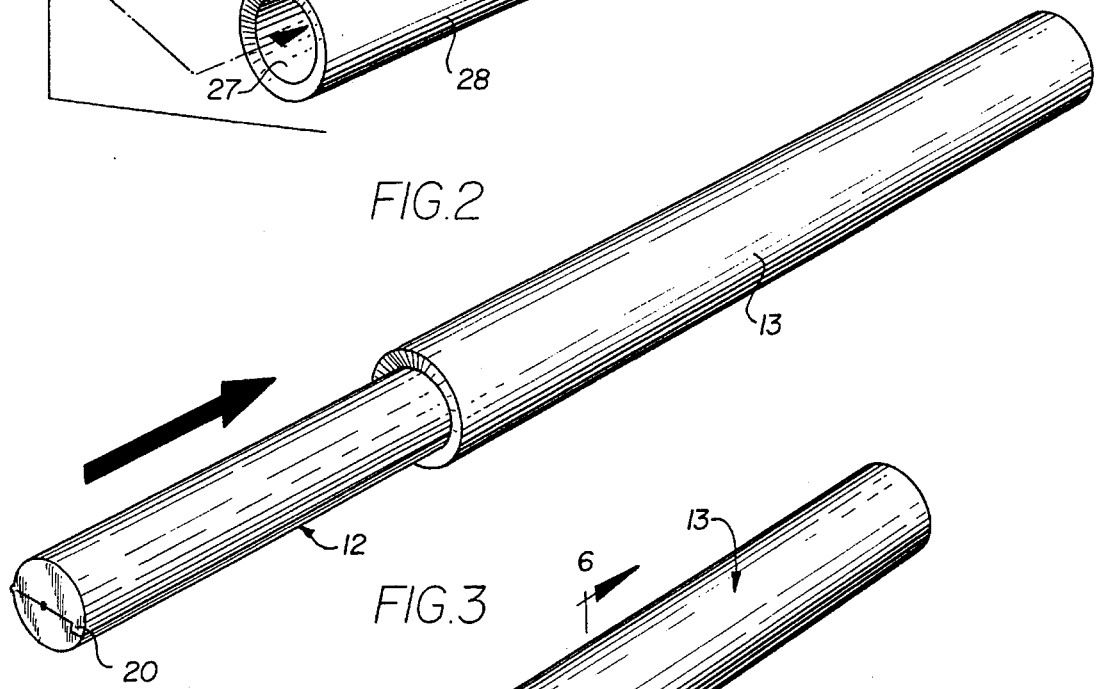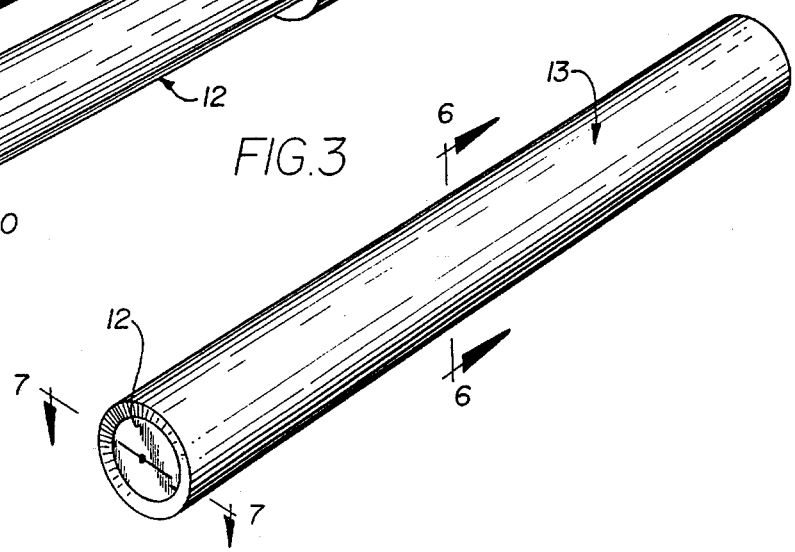

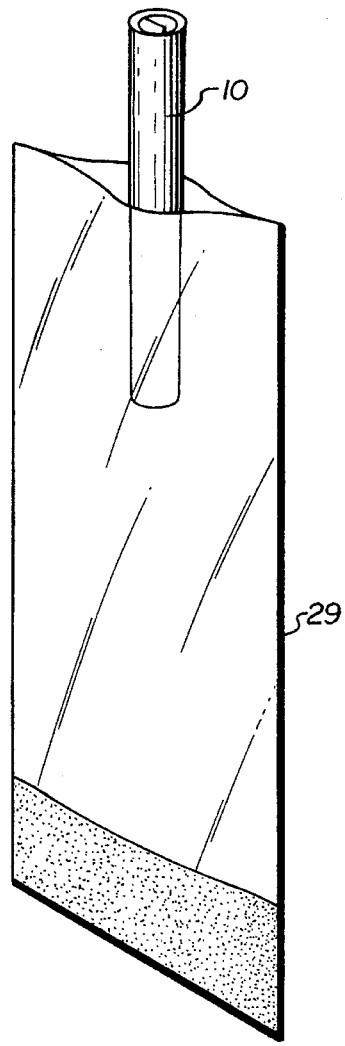
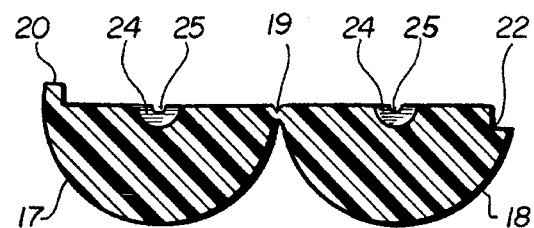
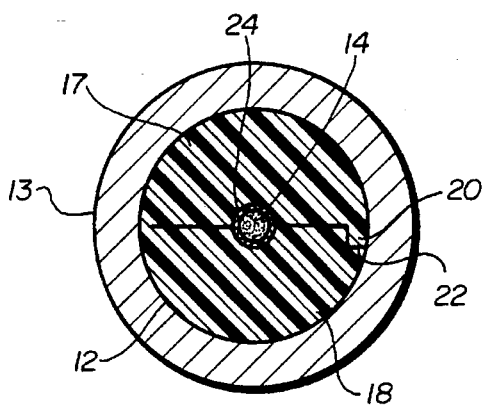
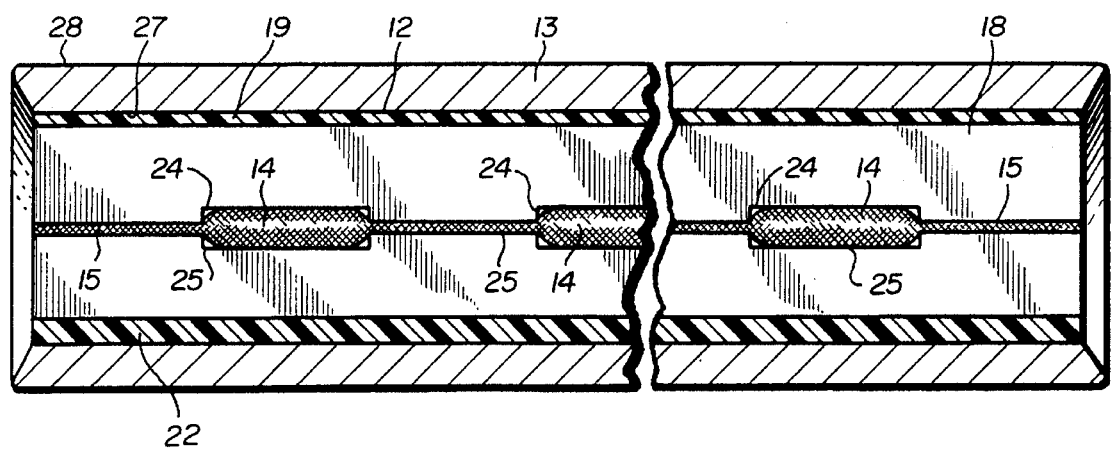

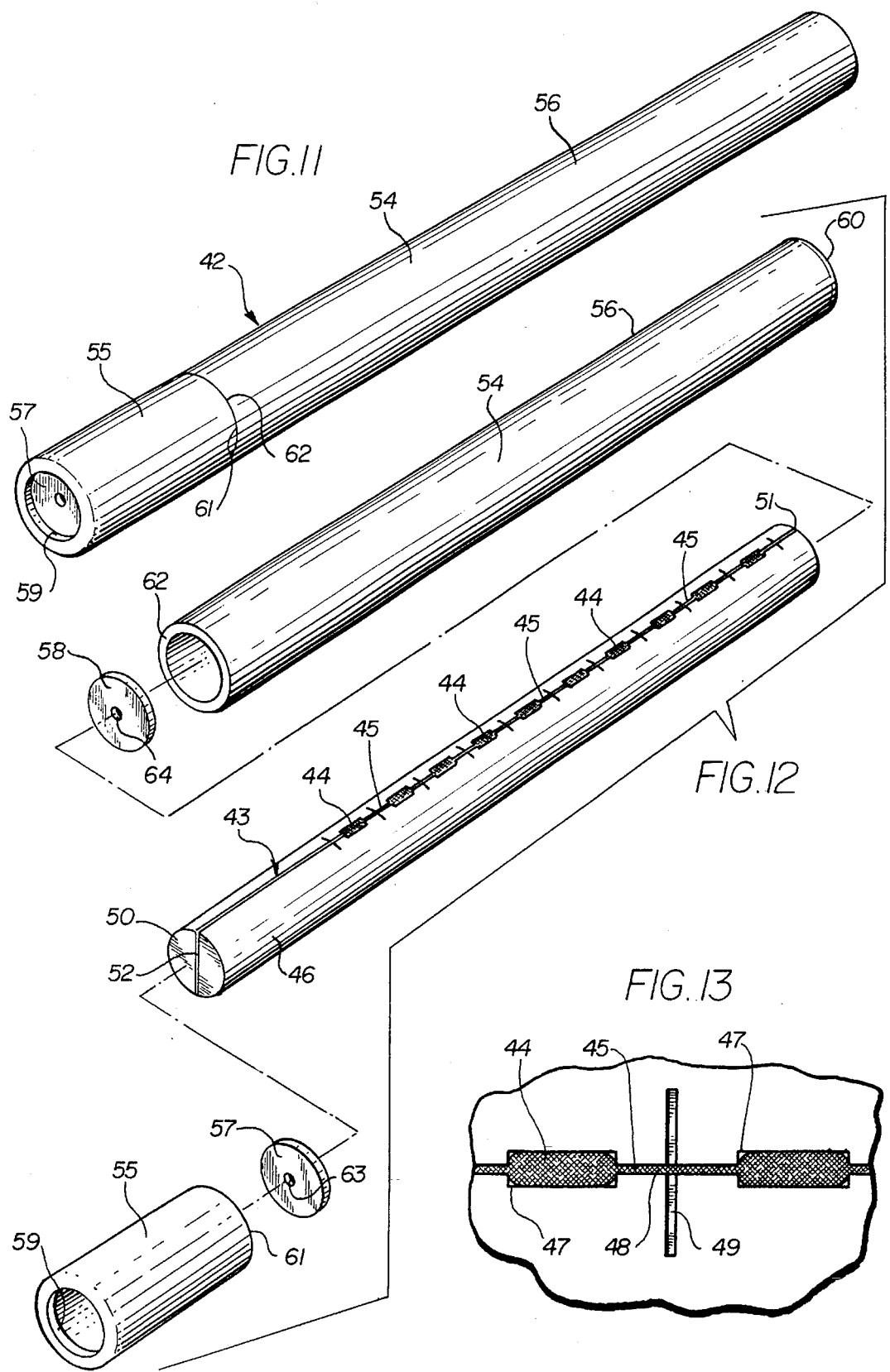

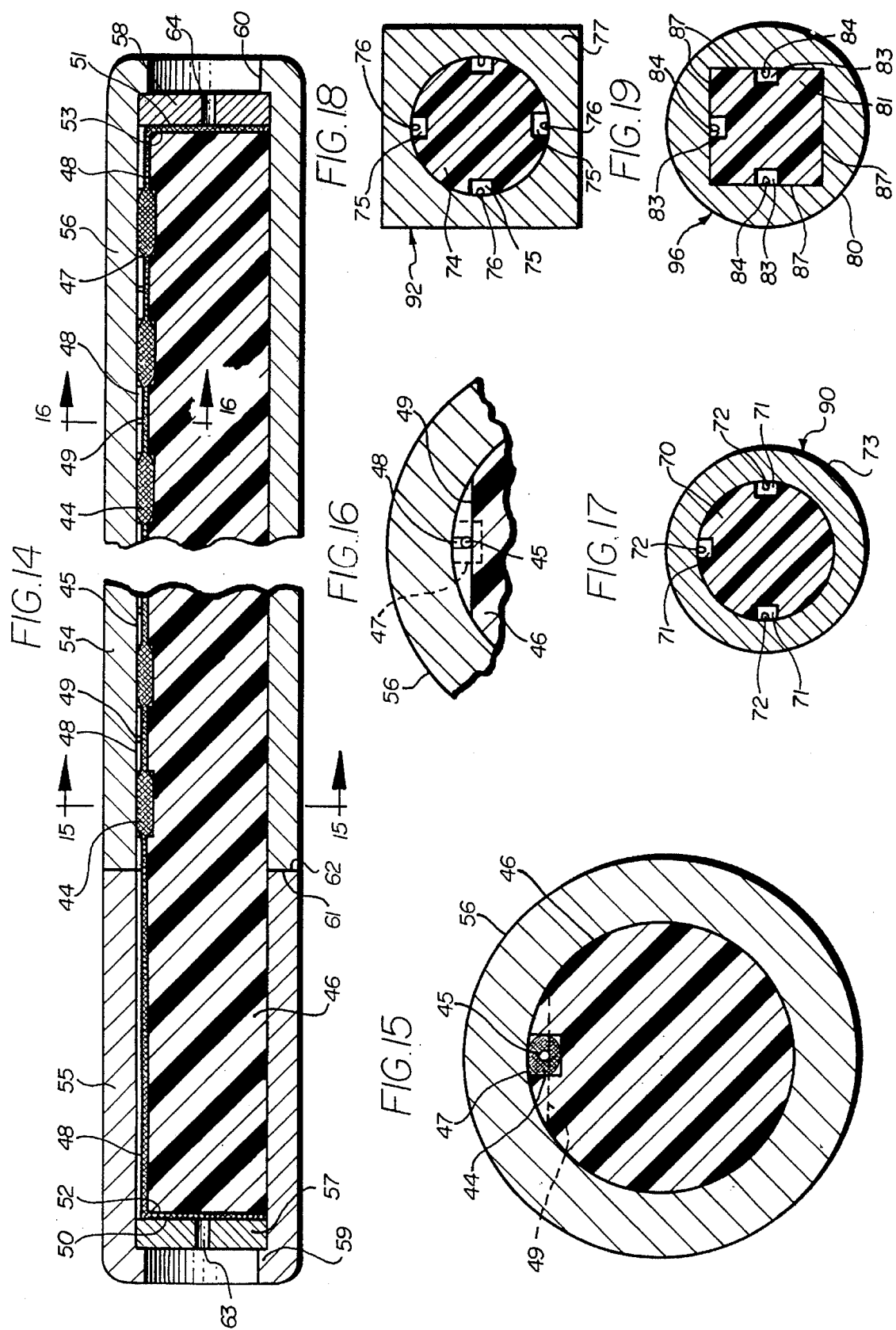

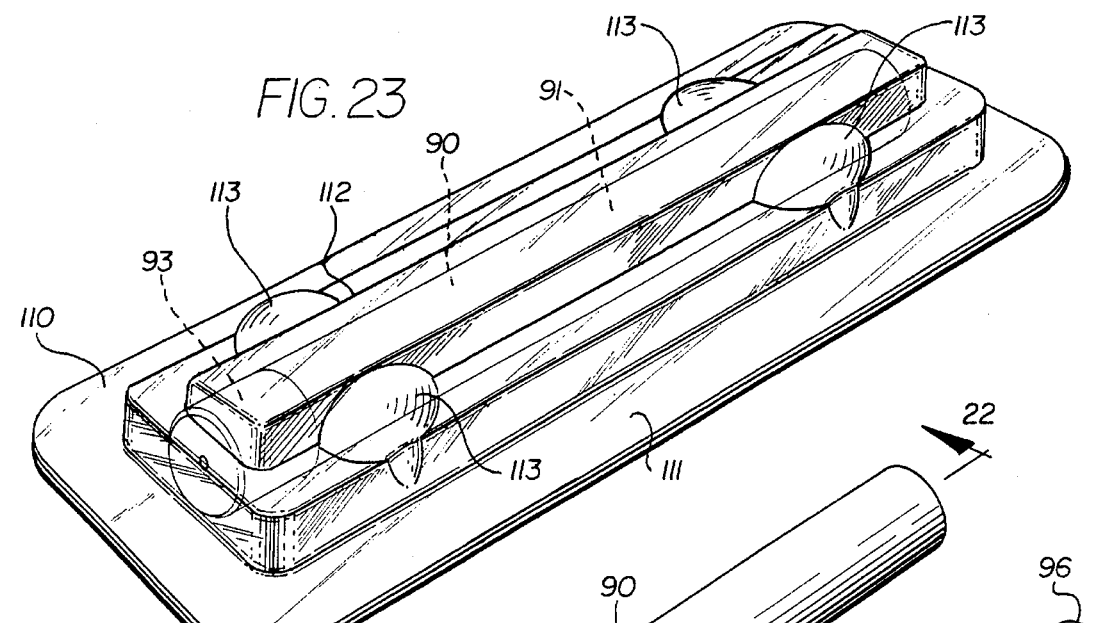
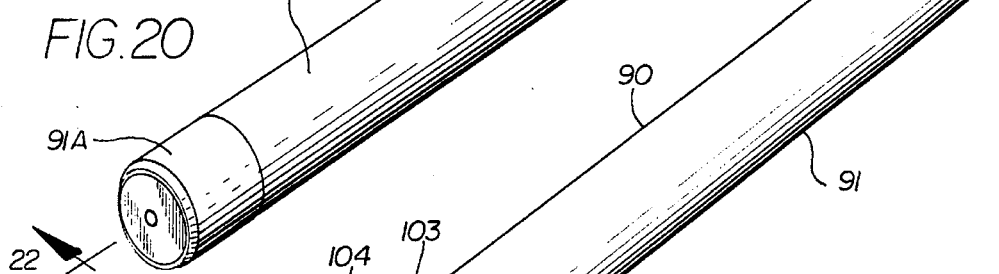
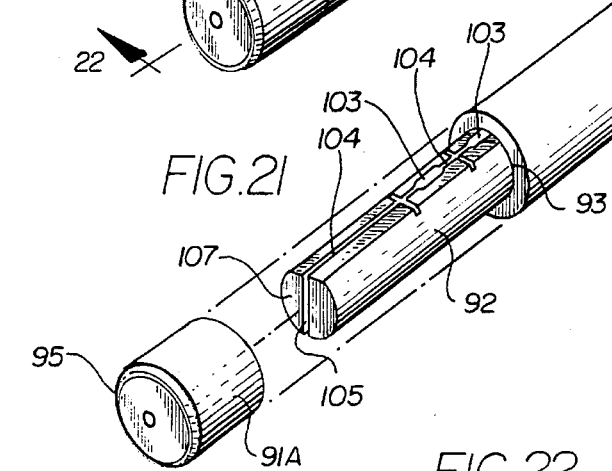
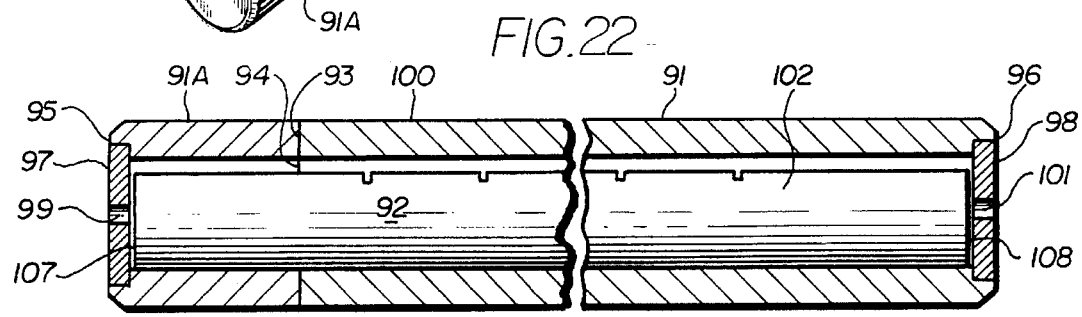

APPARATUS AND METHOD FOR MAKING CARRIER ASSEMBLY FOR RADIOACTIVE SEED CARRIER

FIELD OF INVENTION

The invention relates generally to a carrier assembly and method for preparing the carrier assembly for a delivery system for interstitial radiation therapy and, more particularly, to a carrier assembly in which an elongated member having radioactive seeds therein is disposed. The carrier assembly is heated to provide a semi-rigid elongated member with the carrier assembly being adapted to be shipped to a site of use at which time the semi-rigid elongated member and seeds may be removed from the carrier assembly for use in interstitial radiation therapy.

BACKGROUND OF THE INVENTION

In interstitial radiation therapy, one method for treating tumors is to permanently place small, radioactive seeds into the tumor site. This method is currently accomplished by one of the following two procedures: (a) loose seeds are implanted/placed in the target tissue. The loose seeds, however, are dependent on the tissue itself to hold each individual seed in place during treatment; and (b) seeds are contained within a woven or braided absorbable carrier such as braided suture material.

Currently, the commercially available carrier materials are soft, essentially deflecting materials intended to be pulled through the tissue as opposed to being pushed through the material. The carrier with the seeds disposed therein is secured in place as a single unit, as opposed to one or more individual seeds being held in place, with the plurality of the seeds being held together in the target tissue.

To minimize radiation during handling and shipping, the carrier material with the radioactive seeds therein has been shielded by placing the carrier material and seeds in a curved stainless steel metallic tube ring which attenuates more than 99.9% of the I-125 photons. See U.S. Pat. No. 4,697,575 and European Patent Publication Number 0064,860 published 17.11.82, Bulletin 82/46.

What is desired in using an elongated material having radioactive seeds spaced throughout the material is that the material be sufficiently rigid as to be "non-deflecting." "Non-deflecting" is defined as meaning a delivery system comprising an elongated material, which is absorbable in the living tissue, and having spaced radioactive seeds disposed therein, which has sufficient rigidity to be inserted into a living body near or into a tumor without substantial deflection of the elongated material to provide controlled and precise placement of the radioactive seed material.

While semi-rigid bio-absorbable materials with spaced radioactive seeds are known for use as interstitial implants, they are not entirely satisfactory for relatively large-scale commercial operations. In one instance, the elongated material was made using a bio-absorbable material made of an Ethicon Vicryl® material. Radioactive seeds and teflon spacers were inserted into the material. Needles loaded with the seeds in the carrier material were sterilized or autoclaved causing contraction of the carrier material resulting in a rigid column of seeds and spacers. "Ultrasonically Guided Transperineal Seed Implantation of the Prostate: Modification of the Technique and Qualitative Assessment of Implants" by Van't Riet, et al., International Journal of Radiation Oncology, Biology and Physics, Vol. 24, No. 3, pp. 555–558, 1992.

Another system for providing a semi-rigid elongated material having radioactive seeds disposed therein is disclosed in U.S. Pat. No. 4,697,575 in which a plurality of capsules formed of encapsulated radioactive seeds are positioned in a predetermined array. The seeds are formed into individual, encapsulated capsules, each capsule having a projection on one capsule end and a complementary recess on the remaining capsule end. A projection in one capsule is engageable with a recess in an adjacent capsule such that the desired number of seeds can be plugged together to form a column of rigid bio-absorbable elongated material. This system is not entirely satisfactory inasmuch as it is time consuming to carry out the manipulative plugging steps in assembling a strand of elongated material. One feature desired for a semi-rigid strand is that it be assembled relatively easily and efficiently.

Another feature which is particularly important and desired in providing a semi-rigid bio-absorbable material and seeds is that the radioactive seeds be maintained at a fixed and controlled center-to-center spacing between seeds. It has been found that, in some instances, maintaining the proper spacing between seeds is not always achieved.

What is desired is to provide a semi-rigid bio-absorbable carrier material having seeds disposed within the material with the seeds being accurately spaced a predetermined distance from one another, e.g., 1 centimeter center to center. It is further desired to be able to manufacture the semi-rigid seed carrier in an efficient and relatively expeditious manner to avoid time consuming process steps.

Moreover, it is desired to transport the semi-rigid seed carrier, as a sterile unit, from the manufacturer directly to the site of use in a manner that the carrier is not contaminated by foreign objects and the carrier can be removed from an assembly in a relatively easy manner.

SUMMARY OF THE INVENTION

The invention disclosed and claimed herein serves to obviate problems associated with semi-rigid seed carriers previously described and also achieves the desires sought for a semi-rigid bio-absorbable material having radioactive seeds spaced throughout the material.

Briefly, the present invention utilizes a delivery system in which radioactive seeds are disposed in a flexible, conventional, elongated member made of a suitable bio-absorbable material.

The elongated material and seeds are placed in a spacing jig member which has a plurality of spaced, first and second recesses. The bio-absorbable, elongated material, generally in the form of a flexible, braided string, is disposed in the first recesses while radioactive seeds, which are spaced along the string material, are disposed within the second recesses. The second recesses are spaced a predetermined distance from one another.

A tubular sheath shielding member having inner and outer surfaces slides over the jig member with at least a portion of the spacing jig member contacting the inner surface of the sheath member to maintain the elongated material and seeds in the recesses in which they are deposited. The entire assembly is then heated which causes the elongated material holding the seeds to become semi-rigid. Following the heating process, the bio-absorbable material, upon cooling, will shrink or contract a certain amount; however, the seeds are maintained in their desired position within the second recesses of the jig. The entire assembly then is placed within its primary package container. The primary package container preferably consists of two parts, a commercially available medical grade polymer package manufactured to provide a custom-fit cavity, and, a "breathable" cover which seals the unit while allowing for sterilization gases (such as steam or ethylene oxide) to permeate the cover. Once the carrier assembly is placed in the cavity, the cover is placed on top of the package and sealed thereto. The entire assembly within the sealed primary package container then is sterilized by gas (such as ethylene oxide) or gamma irradiation. It is also contemplated that the unit can be both heated/stiffened and sterilized by using an appropriate autoclave cycle, thus producing a "one step" manufacturing process.

The sterile carrier assembly which comprises the semi-rigid carrier made up of the bio-absorbable elongated material and seeds along with the jig member and sheath contained within the sealed primary package container, then is shipped as a single unit to a particular hospital or application site. At the site, the package is opened; the carrier assembly is removed from the package; the sheath member is removed exposing the jig; and, one or more of the seeds in the non-deflecting material is removed from the jig member and loaded into a conventional, hollow, metal dispensing needle or applicator cartridge which then is used to implant the radioactive seeds into or contiguous to a tumor being treated.

DESCRIPTION OF THE DRAWINGS

Further advantages of the invention will become apparent upon a reading of the following detailed description taken in conjunction with the accompanying drawings in which:

FIG. 1 shows a perspective view of one embodiment of the carrier assembly of the present invention comprising a flexible, elongated seed carrier having spaced, radioactive seeds disposed therein, a hinged jig member having a plurality of spaced, first and second recesses into which the seed carrier is adapted to be loaded, and a sheath shielding member into which the loaded jig member is adapted to be inserted;

FIG. 2 shows a loaded jig being inserted into a sheath member;

FIG. 3 shows the carrier assembly of the present invention with the sheath member covering the jig member which, in turn, houses an elongated bio-absorbable material and a plurality of spaced radioactive seeds;

FIG. 4 shows the carrier assembly of the present invention following the heating process being inserted into one embodiment of a shipping container or package;

FIG. 5 shows a section view of the hinged jig member taken along lines 5—5 in FIG. 1;

FIG. 6 shows a section view of a seed carrier and jig member disposed within a sheath member taken along lines 6—6 in FIG. 3;

FIG. 7 shows a plan section view of a seed carrier loaded in the first and second recesses of the spacing jig member taken along lines 7—7 in FIG. 3;

FIG. 11 shows a further embodiment of the carrier assembly of the present invention in which a sheath member comprising multiple components, encloses a jig member which has a seed carrier disposed in recesses located on the wall surface of the jig member;

FIG. 12 shows the unassembled components of the carrier assembly of FIG. 11;

FIG. 13 shows a partial, exploded view of the elongated seed carrier material and seeds located in first and second recesses of the jig member shown in FIG. 12 with a knife edge slot traversing the first recess;

FIG. 14 shows a vertical, section view of the carrier assembly of FIG. 11 in an assembled position;

FIG. 15 shows an end section view taken along lines 15—15 in FIG. 14 in which a radioactive seed is disposed in a second recess located in the jig member wall;

FIG. 16 shows a partial, fragmentary end section view taken along lines 16—16 in FIG. 14 in which elongated carrier material is disposed in a first recess located in the jig member wall;

FIG. 17 shows a further modification of the jig member of the present invention in which three seed carriers, each including bio-absorbable, elongated material and spaced seeds disposed therein, are disposed in three, spaced complementary first and second recesses located on the wall surface of the jig member with the carrier assembly being elliptically-shaped;

FIG. 18 shows a further modification of the present invention in which four separate seed carriers are mounted in four, spaced sets of first and second recesses located on the wall surface of the jig member with the outer wall surface of the sheath member having a square shape;

FIG. 19 shows a still further embodiment of the present invention in which the wall surface of the jig member is square and frictionally engageable with a mating square-shaped inner wall surface of a sheath member while the outer sheath member wall surface is circular-shaped;

FIG. 20 shows yet another embodiment of the carrier assembly of the present invention in which a sheath member comprising two components encloses a jig member which has a carrier assembly disposed in recesses located on the wall surface of the jig member;

FIG. 21 shows the carrier assembly of FIG. 20 with one sheath component disassembled from the jig member;

FIG. 22 shows a vertical, section view of the carrier assembly of FIG. 20 taken along lines 22—22 in FIG. 20; and, FIG. 23 shows the carrier assembly of FIG. 20 disposed with a primary package container.

DETAILED DESCRIPTION

Figure 8:
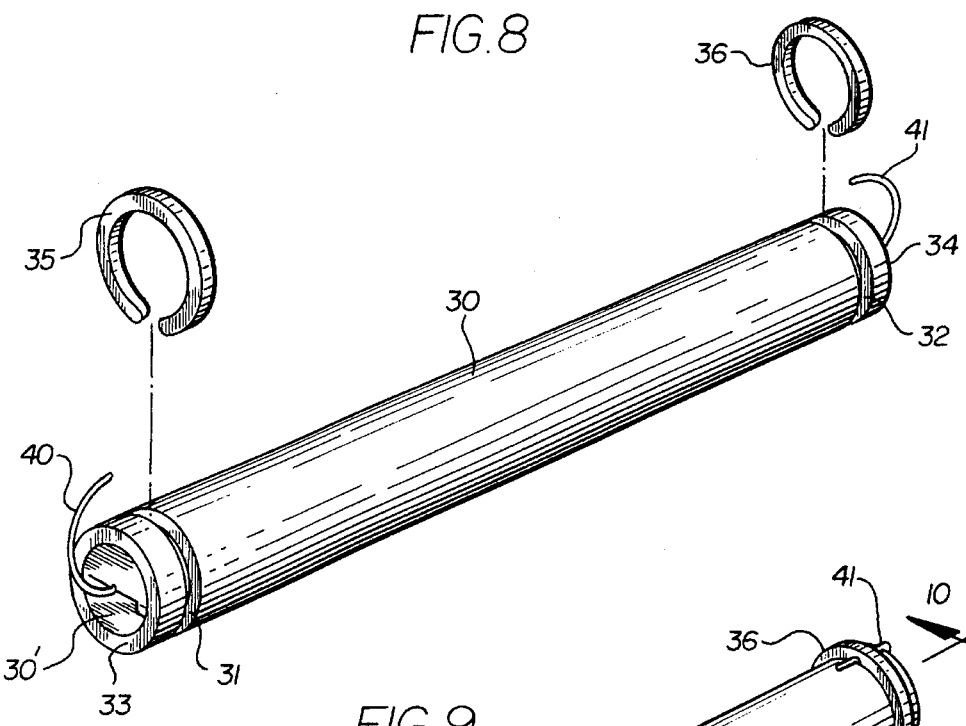
FIG. 8 shows a perspective view of another embodiment of a seed carrier assembly of the present invention in which snap washer rings, shown in an unassembled condition, serve to hold the elongated bio-absorbable seed carrier material in tension.

Referring to the drawings, one embodiment of the invention shows carrier assembly 10 which comprises a seed carrier 11, jig member 12 and shielding sheath member 13. Seed carrier 11 comprises a plurality of radioactive seeds 14 which are disposed within an elongated bio-absorbable carrier material 15 whose length is substantially longer than its width. The radioactive seeds can be made in any suitable manner. The seeds of the present invention may contain any suitable radiation source capable of emitting radiation having therapeutic properties. Such sources and their preparation and use are well-known to those skilled in the art. By way of example only, gamma ray emitting elements such as radon and radium may be employed, as may the radioactive forms of various metals such as cesium, cobalt, gold, iridium, palladium (Pd-103), samarium and tantalum. Other substances and compounds, including mixtures of one or more radiation sources capable of emitting therapeutically useful forms of radiation (i.e. gamma rays, alpha particles, beta particles, electrons neutrons, electromagnetic waves, etc.) are also contemplated as useful in the practice of the present invention, provided they are presented in a form and at concentrations or amounts which preserve the overall clinical health of a patient.

One seed presently available is Model No. 6711 available from Medi-Physics, Inc., an Amersham Company located in Arlington Heights, Ill., U.S.A. and referred to in Medi-Physics Bulletin No. TTO893A. The radioactive seeds are each welded titanium capsules containing I-125 absorbed onto a silver rod. The product, which is available from Amersham Holdings, Arlington Heights, Ill., is commercially known as I-125 Seeds®.

Seeds 14 are spaced at predetermined dimensions in an elongated bio-absorbable material 15 whose length is substantially longer than its width. The carrier material is a flexible material and is absorbable in a living body. The material may be made of any of the natural or synthetic materials absorbable in a living body. Examples of natural absorbable materials as disclosed in U.S. Pat. No. 4,697,575 are the polyester amides from glycolic or lactic acids such as the polymers and copolymers of glycolate and lactate, polydioxanone and the like. Such polymeric materials are more fully described in U.S. Pat. Nos. 3,565,869, 3,636,956, 4,052,988 and European Patent Application 30822. Specific examples of absorbable polymeric materials that may be used to produce the substantially non-deflecting members of the present invention are polymers marketed by Ethicon, Inc., Somerville, N.J., under the trademarks "VICRYL" and "PDS".

The absorbable material should preferably maintain its integrity for from 1 to about 14 days. Preferably the material should be absorbed in living tissue in a period of time of from about 70 to 120 days. It is preferred that as little absorbable material as possible be used in the delivery systems of the present invention.

One seed carrier contains 10 No. 6711 I-125 Seeds® spaced at 1 cm. (center to center) within a braided absorbable carrier. The carrier material is Ethicon No. 1 Vicryl® Synthetic Absorbable Suture (Polyglactic 910). The seed carrier commercially known as product code 6720, I-125 Seeds® In Carrier, and is available from Medi-Physics, Inc., Arlington Heights, Ill. 60004.

Spacing jig 12 shown in the embodiment of FIG. 1 comprises cylindrical member 16 which includes two complementary jig sections 17, 18 hinged together at 19. Jig section 17 includes a boss 20 which extends along the length of jig edge 21. Boss 20 is adapted to seat in groove 22 which extends along the length of edge 23 of jig section 18. Jig section 17 is adapted to close upon jig section 18 by pivoting section 17 about hinge 19 in the direction of arrow "A" whereby, as seen in FIGS. 1 and 2, boss 20 seats in groove 22.

Spacing jig 12 is made of any suitable medical grade material, such as a plastic material made by Polymer Corp., Reading, Pa., number Ultem 1000F, or other materials of choice. It must be able to withstand the temperatures to which the assembly will be subjected to stiffen the bio-absorbable material, e.g., dry heat of 150° C.–185° C. or 1 hour, 120° C.–125° C., 210 k Pa; and, it also must be sufficiently rigid to maintain its shape.

Jig section 17 has a plurality of spaced, first recesses 24 which extend along the length of the longitudinal axis of jig 12 when jig sections 17, 18 are in the closed position shown in FIG. 2. A plurality of second recesses 25, which are spaced from one another but which connect with the first spaced recesses 24, as seen in FIG. 1, also extend along the longitudinal axis of jig section 17. Complementary first and second recesses 24, 25 are located along the length of jig section 18 as seen in FIG. 1. Upon closure of jig sections 17, 18, recesses 24, 25 in jig section 17 align with corresponding recesses 24, 25 in jig section 18.

Seeds 14 are adapted to be deposited or accommodated in recess 24 whereas the flexible, elongated, bio-absorbable material 15 is adapted to seat or be accommodated in recesses 25 as seen more clearly in FIG. 7. Seeds 14 are maintained in the predetermined spaced positions at all times in the carrier assembly inasmuch as once seeds 14 are deposited in appropriate recesses 24 in jig member 12, and jig member 12 is inserted in sheath member 13, seeds 14 cannot be moved out of the recesses in any direction beyond the dimensions of recesses 24.

Sheath member 13 comprises a tubular member having inner sheath surface 27 and outer sheath surface 28. The tube is of a length sufficient, when installed over jig member 12, to cover all recesses 24, 25. Preferably, the sheath member is at least equal in length to the length of spacing jig 12 and, most preferably, the outer sheath surface extends in length slightly beyond the inner sheath surface as seen in FIG. 7. Sheath member 13 is made of medical grade stainless steel. The inner diameter of sheath member 13 is slightly larger than the outer diameter of jig member 12 so that, upon assembly, a slidable, friction fit exists between members 12 and 13 whereby, when the fully assembled carrier assembly is held in a vertical position, as seen, for example, in FIG. 4, jig member 12 is maintained by friction in sheath member 13.

In assembly, a strand of flexible, elongated bio-absorbable material 15 with spaced radioactive seeds 14 disposed therein is inserted in the appropriate recesses 24, 25 of jig section 18. Jig section 17 then is closed over jig section 18 whereby the recesses 24, 25 in section 17 close over the elongated carrier material and seeds. Jig member 12 loaded with seed carrier 11 then is inserted into tubular sheath member 13 to form completed carrier assembly 10.

Assembly 10 then is dry heated. The dry heat causes the seed carrier to become substantially rigid or non-deflecting.

Following the heating process, the unitary carrier assembly, i.e., spacing jig 12 and shielding sheath 11, is deposited in a container or pouch such as illustrated at 29 shown in FIG. 4 or the preferred container 110 shown in FIG. 23. Pouch 29 or container 110 then is sealed to completely enclose the carrier assembly for sterilization by ethylene oxide gas or gamma radiation. Then the assembly is shipped to a customer or site of use.

Figure 9:
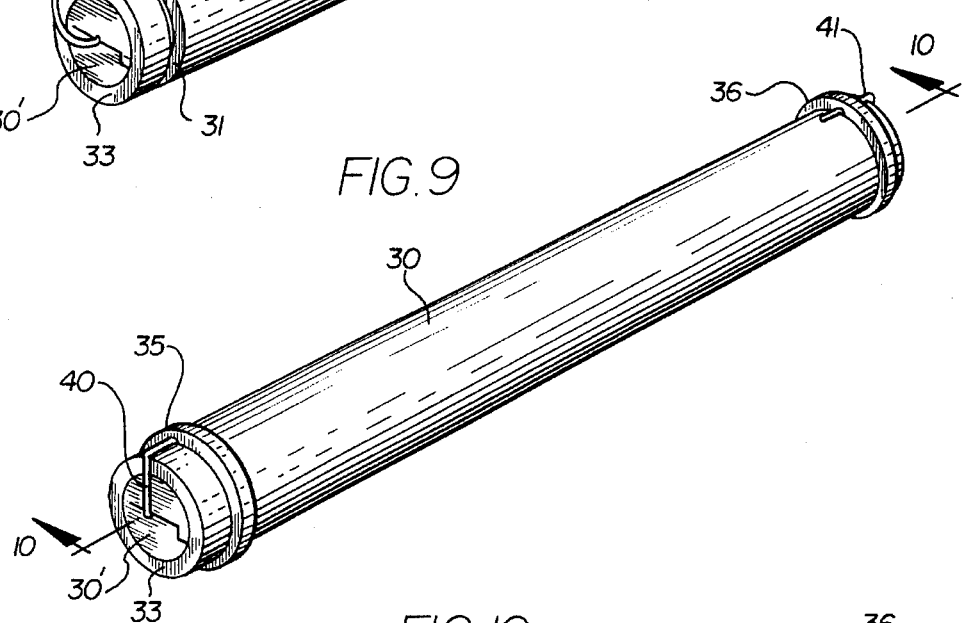
FIG. 9 shows the seed carrier assembly of FIG. 8 with the snap rings inserted in position on respective ends of the sheath member.
Figure 10:
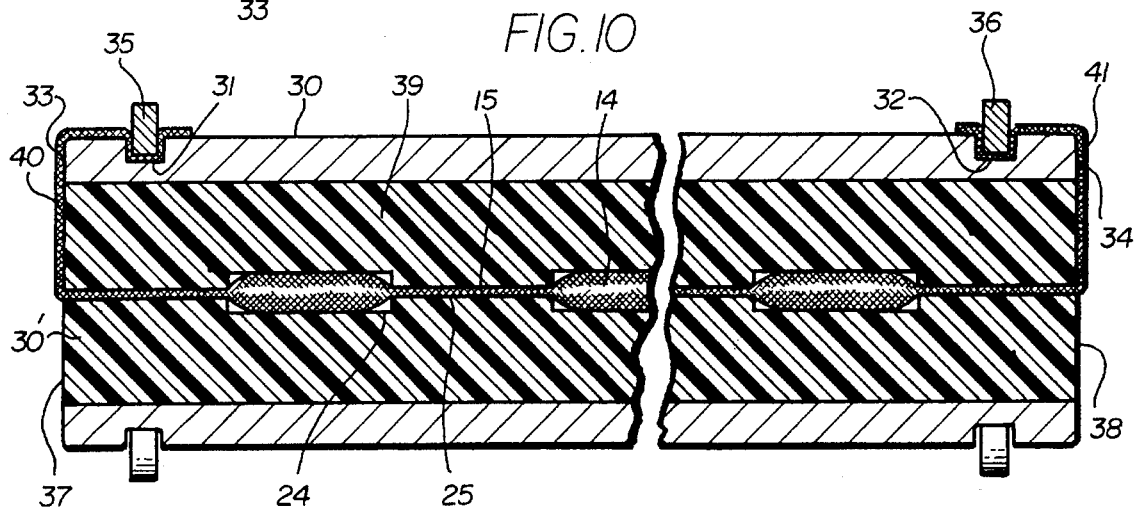
FIG. 10 shows a section view taken along lines 10—10 in FIG. 9 in which the elongated seed carrier material is maintained in tension by the snap rings.

FIGS. 8–10 show another embodiment of the seed carrier assembly of the present invention. In this particular embodiment, tubular sheath member 30 is disposed over hinged jig member 30'. Sheath member 30 has grooves 31, 32 disposed in its outer wall contiguous to sheath member ends 33, 34. A conventional plastic or metal snap ring 35 is adapted to seat in groove 31 whereas snap ring 36 is adapted to seat in groove 32.

Upon assembly, seed carrier 11 comprising seeds 14 and elongated carrier material 15, is positioned in respective recesses 24, 25. The elongated material in this particular embodiment is of a length such that the ends of the material extend beyond the respective ends 37, 38 of spacing jig member 39. Each material end 40, 41 is pulled manually upward and folded over the outer wall surface of sheath member 30, the respective material ends 40, 41 being pulled to place tension on the material ends. Material end 40 is of a length sufficient to permit it to be positioned in sheath groove 31. Similarly, material end 42 is of a length sufficient to permit it to extend across sheath groove 32. Snap ring 35 then is inserted into groove 31 and snap ring 36 is inserted into groove 32 as seen in FIG. 9 whereby material ends 40, 41 are held under tension in grooves 31, 32. With this embodiment of the invention, tension placed on material ends 40, 41 serves to preclude the flexible material ends from contracting upon heating or autoclaving during which a semi-rigid carrier material is formed.

FIGS. 11–16 illustrate a further embodiment of the invention, this embodiment being more preferred than the embodiment of FIGS. 1–10, whereas the embodiment of FIGS. 20–22, inclusive, represents the most preferred embodiment of the invention. FIG. 11 shows carrier assembly 42 which includes: (i) seed carrier 43, which includes a plurality of seeds 44 spaced at predetermined locations in bio-absorbable elongated carrier material 45, (ii) spacing jig 46, and (iii) shielding sheath member 50.

Jig member 46 is a single piece, cylindrical-shaped plastic member having first recesses 47 in which seeds 44 are adapted to be inserted, and second recesses 48 into which elongated material 45 is inserted. The first and second recesses are aligned along the longitudinal length as shown in FIG. 12. Recess 48 terminates into vertical recesses 52, 53 which traverse the respective jig member ends 50, 51. Accordingly, carrier material 45 seats in recesses 48, 52 and 53 as seen more clearly in FIG. 14.

A plurality of spaced slots 49 traverse recess 48. Each slot is of a size to receive a portion of a cutting blade or knife edge (not shown) suitable to slice or cut through elongated carrier material 45. Slots 49 preferably are spaced 1 cm. to 1 cm., center to center, so that a desired portion of seed carrier 43 may be removed from the jig member for a particular application while the remaining portion of seed carrier 43 is retained in jig member 46 until a further implant application is required.

Sheath member 54 comprises two tubular sections 55, 56 and two washer members 57, 58, the latter being adapted to be inserted in sheath member sections 55, 56 respectively.

Sheath section 55 is a stainless steel, tubular-shaped member having one of its two ends 59 flanged inwardly. Similarly, tubular-shaped sheath section 56, which is longer in length than sheath section 55, also is inwardly flanged at one of its two ends 60. Upon assembly, washer 58 is disposed in tubular section 56 and seats against sheath flange 60 to substantially close one end of sheath section 60. Washer 57 is disposed within tubular section 55 and seats against sheath flange 59 to substantially close one end of sheath section 55. When sheath sections 55, 56 are brought together, the remaining sheath section ends 61, 62 abut one another as seen in FIGS. 11 and 14.

Upon assembly, seed carrier 43 is loaded in first and second recesses 47, 48, 52 and 53 of jig member 46. Washer 58 is positioned against sheath flange 60 in sheath section 56. The loaded jig member is inserted into sheath section 56 until jig member end 51 abuts the inner wall surface of sheath washer 58. Washer 57 is inserted in tubular sheath section 55 and abuts sheath flange 59. Sheath member 55 then is inserted over jig member 46 until jig end 52 of jig section 55 abuts the inner wall surface of sheath washer 57 and the remaining sheath section ends 61, 62 abut one another. As in the case of the embodiments discussed previously, sheath members 55, 56 are slidably, frictionally engageable with jig member 46 and will remain seated thereon when the assembly is placed in a vertical position.

Further, recesses 47, 48, 52 and 53 are of a depth that when the elongated carrier material 45 and seeds 44 are disposed therein, the carrier and seeds preferably will not, upon assembly, contact the inner wall surface of the sheath member sections 55, 56.

Sheath washers 57 and 58 each have a small opening 63, 64 respectively, the openings serving to permit fluid to escape from sheath member 54 during an autoclaving or heating process. It is appreciated that while sheath member 54 has been formed of four components, two sheath member sections and two washers, one could, if desired, form each sheath section to have an inward flange at one end so that the washers 59 and 60 could be eliminated.

FIGS. 17–19 show other modifications of the invention. Referring first to FIG. 17, jig member 70 employs three, spaced sets of first and second recesses 71, 72 displaced at 0°, 90° and 270° on the outer jig wall surface. Each set of first and second recesses 71, 72 is disposed along the length of the jig member wall surface as previously discussed with respect to the jig member embodiments of FIGS. 1 and 12. In this instance, a plurality of seed carriers (three) can be assembled, autoclaved and shipped as a unit in carrier assembly 90. Jig member 70 is shown as being elliptically-shaped and is adapted to be inserted into an elliptically-shaped sheath member 73.

The embodiment of FIG. 18 discloses a carrier assembly 92 which utilizes a jig member 74 having four sets of first and second recesses 75, 76 spaced at 0°, 90°, 180° and 270° for receiving four seed carriers. In this instance, the outer wall surface of sheath member 77 is square-shaped while the inner wall surface is circular-shaped to mate with the circular shape of jig member 74.

FIG. 19 discloses an embodiment of a seed carrier assembly 96 in which sheath member 80 has a circular outer wall surface and a square-shaped inner wall surface which is slidably, frictionally engageable with the square-face outer wall surface of jig member 81. Jig member 81 utilizes three sets of first and second recesses 83, 84, one set being located on each of three of the four wall surfaces 87 of jig member 81.

FIGS. 20–22, inclusive, show yet a further and most preferred embodiment of the invention. FIG. 20 shows a carrier assembly 100 which includes sheath member 90 which comprises two components, a first sheath component 91 which serves as a receptor for the majority of spacing jig 92 and a second sheath component 91A which serves as a cap for that portion of spacing jig 92 which extends outward from first sheath component 91. Components 91, 91A are tubular members having open ends 93, 94 at one end of the respective components. The remaining respective component ends 95, 96 are recessed, FIG. 22, to receive plugs 97, 98. Plugs 97, 98 each have small openings 99, 101 for any exhaust gases which are generated either in heating or autoclaving the carrier assembly 100. Plugs 97, 98 are press fitted into the respective recesses to provide a capped end at each end of the assembled carrier assembly 100.

Spacing jig 102 is similar to spacing jig 46 and includes a plurality of spaced first recesses 103 for receipt of carrier seeds 44 and second recesses 104 for receipt of elongated carrier material 45. The first and second recesses are aligned along the longitudinal length. Recess 104 terminates at each end of the jig 102 into recesses 105, only one of which is shown, which traverse the respective jig member ends 107, 108. Upon assembly, jig member end 107 is contiguous to plug 97 whereas jig member end 108 is contiguous to plug 98.

Jig member 92 preferably is formed of a ⅜" outside diameter Ultem 1000 stock rod available from Polymer Corporation, Reading, Pa. Sheath component members 91, 91A are formed from ⅝"×11" gage (0.120 inch wall), No. 304 stainless steel tubing. Plug members 97, 98 are each ½" outside diameter stock, No. 304 stainless steel rounds having a small opening therein suitable to permit the release of gases generating in any heating or autoclaving step.

FIG. 23 shows primary package container 110. Container 110 consists of two parts, a first, transparent, member 111 made from a commercially available medical grade package polymer. Member 111 is shown in a position, which is upside down of its normal position in which carrier assembly 90 is disposed in cavity 112. A plurality of finger grip openings 113 are positioned on each side of cavity 112 so that upon opening container 110, an individual's fingers can be placed in a pair of openings 113 to grasp carrier assembly 90 and remove it from container 110. A breathable cover 114 normally is disposed over member 111 once carrier assembly 90 is seated in cavity 112. Cover 114 serves to cover and seal carrier assembly 90 in cavity 112 and also allows for sterilization gases, such as steam or ethylene oxide, to permeate the cover material. Once the carrier assembly is placed in cavity 112, cover 114 is seated on top of member 111 and sealed in place. Once the carrier assembly is within the sealed package container 110, the entire assembly then is heated which causes the elongated carrier material holding the seeds to become substantially rigid or non-deflecting.

While one or more embodiments of the invention have been herein illustrated and described in detail, it will be understood that modifications and variations thereof may be effected without departing from the spirit of the invention and the scope of the appended claims.

What is claimed is:

1. A carrier assembly containing radioactive seeds disposed within a bio-absorbable carrier material which is adapted to be inserted into a living tissue, said carrier assembly comprising:

a seed carrier comprising an elongated member made of a carrier material absorbable in a living tissue and having a length substantially longer than its width;

a plurality of predeterminedly spaced radioactive seeds disposed within said elongated member;

a jig member having a plurality of first and second recesses therein, said first recesses having a shape to receive said seeds and said second recesses having a shape to receive said seed carrier; and, a removable sheath member disposed over said jig member, said sheath member having inner and outer surfaces, said inner sheath member surface being in slidable contact with at least a portion of said jig member;

whereby, in use, said sheath member is disengageable from said jig member and at least a portion of said elongated member including at least one seed is removable from said jig member.

2. A carrier assembly in accordance with claim 1 in which said elongated member is non-deflecting.

3. A carrier assembly in accordance with claim 1 in which said jig member includes a plurality of spaced sets of first recesses and second recesses extending along the length of said jig member.

4. A carrier assembly in accordance with claims 1 or 3 wherein said jig member has at least one slot traversing one of said second recesses.

5. A carrier assembly in accordance with claim 4 wherein said jig member has a plurality of spaced slots traversing said second recesses.

6. A carrier assembly in accordance with claim 5 wherein said slots are spaced an equal distance from one another.

7. A carrier assembly in accordance with claim 6 wherein each of said slots is spaced an equal distance from one of said first recesses.

8. A carrier assembly in accordance with claim 1 in which said jig member has a longitudinal axis and comprises two sections, each section having a plurality of first and second recesses disposed along the length of each section such that when said sections are assembled, said recesses on said first and second jig sections are complementary with each other to form a set of first and second recesses extending along the longitudinal axis of said assembled jig member.

9. A carrier assembly in accordance with claim 8 in which said jig sections are hinged together along the length of said sections.

10. A carrier assembly in accordance with claim 1 wherein said elongated member has two ends and means for placing tension on each of the two ends of said elongated material.

11. A carrier assembly in accordance with claim 10 wherein said sheath member has first and second ends;

a first groove and a second groove located in the outer surface of said sheath member said first groove being contiguous to said first sheath member end and said second groove being contiguous to said second sheath member end;

said elongated member having first and second ends with said first end of said member being located in said first groove and said second member end being located in said second groove; and, means for retaining said material ends in said grooves.

12. A carrier assembly in accordance with claim 11 wherein said retaining means includes snap fasteners inserted into said grooves.

13. A carrier assembly in accordance with claim 1 in which the sheath member outer surface is circular.

14. A carrier assembly in accordance with claim 1 in which the sheath member outer surface is non-circular.

15. A carrier assembly in accordance with claim 1 wherein said jig member has an outer surface which is circular.

16. A carrier assembly in accordance with claim 1 wherein said jig member has an outer wall surface which is non-circular.

17. A carrier assembly in accordance with claim 1 wherein said sheath member comprises two sheath sections each section comprising a tubular member having two ends, one of said ends being flanged inwardly and said remaining end being shaped to abut the corresponding second end of said remaining sheath section whereby said sheath member components enclose said jig member.

18. A carrier assembly in accordance with claim 17 wherein each sheath section further includes a sheath washer disposed in said sheath section and abutting said flanged sheath section end when said carrier assembly is assembled.

19. A carrier assembly in accordance with claims 1 or 18 wherein said sheath member comprises two tubular component members, each sheath component member having two ends with one of said ends being open and said remaining end being substantially closed, one of said component members receiving a portion of said jig member and said second sheath component member receiving said remaining portion of said jig member; and said two sheath components, in an assembled state, enclosing said spacing jig member with said open ends of said sheath component members abutting one another.

20. A carrier assembly for a radioactive seed carrier which is adapted to be inserted into a living tissue, said carrier assembly comprising:

an elongated member made of a material which is absorbable in a living tissue and having a length substantially longer than its width;

a plurality of predetermined spaced radioactive seeds disposed in said elongated member;

a jig member having a first end and a second end and having a plurality of aligned first recesses and second recesses and having a shape in which said first recesses are adapted to receive said seeds and said second recesses are adapted to receive said elongated member;

a sheath member adapted to seat over said jig member and be frictionally retained thereon; and, said sheath member, when assembled on said jig member, having a length which is sufficient to cover at least said first and second recesses in said jig member.

21. A carrier assembly in accordance with claim 20 wherein said jig member has a plurality of slots traversing said first recesses.

22. A carrier assembly in accordance with claim 20 wherein said sheath member comprises two sheath sections, each section being insertable over one of said jig member ends.

23. A carrier assembly in accordance with claim 22 wherein each sheath section has one end thereof substantially closed.

24. A carrier assembly in accordance with claim 23 wherein, upon assembly of said carrier device, said remaining sheath section ends abut one another.

25. A carrier assembly in accordance with claims 1 or 20 and further including a package container into which said assembly is sealed.

26. A carrier assembly in accordance with claim 25 wherein said package includes a first component for holding said carrier assembly and a cover releasably disposed on said first component.

27. The method of forming a carrier assembly for an elongated carrier material which is absorbable in a living tissue and which has at least one radioactive seed disposed within said material, said method comprising:

loading a carrier device comprising a flexible elongated material having at least one radioactive seed therein into a jig member having first recess and second recess, said seed being positioned in said first recess and said elongated material being positioned in said second recess; and, assembling a sheath member having inner and outer surfaces over said loaded jig member whereby at least a portion of said sheath member inner surface contacts said jig member.

28. The method of claim 27 and further including the step of:

heating said carrier assembly sufficiently to provide a non-deflecting elongated material having at least one seed therein when said material and seed are removed from said jig member.

29. The method of forming a carrier assembly in accordance with claims 27 or 28 wherein said jig member has a plurality of spaced first recesses and spaced second recesses, and placing a flexible elongated material having seeds therein into said first and second recesses whereby said seeds are positioned in said spaced first recesses and said elongated material is positioned in said spaced second recesses.

30. The method of claim 29 and further including the step of removing at least a portion of said elongated material and one seed from said member.

31. The method of claim 29 and further including the step of cutting said non-deflecting elongated material while said material is in said jig member and removing a portion of said elongated material and at least one seed from said jig member.

32. The method of claim 28 and further including placing of said assembled carrier assembly into a package container prior to heating said assembly and then heating said assembly and container to form a non-deflected elongated material.

33. The method of claim 32 and further including autoclaving said assembly and package.

* * * * *